(12) United States Patent
Shears et al.

(10) Patent No.: US 7,351,580 B2
(45) Date of Patent: Apr. 1, 2008

(54) USE OF A TRANSGENE ENCODING A VERTEBRATE PHYTASE TO INCREASE CAPACITY TO UTILIZE PHYTIC ACID IN LIVESTOCK FEED

(75) Inventors: Stephen Shears, Chapel Hill, NC (US); Paul R. Reynolds, Mars, PA (US); James N. Petitte, Raleigh, NC (US)

(73) Assignees: North Carolina State University, Raleigh, NC (US); The United States of America, as represented by the Department of Health and Human Services, N.I.H., Washington, DC (US); University of Rochester, Rochester, NY (US)

( * ) Notice: Subject to any disclaimer, the term of this patent is extended or adjusted under 35 U.S.C. 154(b) by 457 days.

(21) Appl. No.: 10/343,339

(22) PCT Filed: Aug. 13, 2001

(86) PCT No.: PCT/US01/25339

§ 371 (c)(1),
(2), (4) Date: Jul. 3, 2003

(87) PCT Pub. No.: WO02/14494

PCT Pub. Date: Feb. 21, 2002

(65) Prior Publication Data

US 2004/0040048 A1 Feb. 26, 2004

Related U.S. Application Data

(60) Provisional application No. 60/224,496, filed on Aug. 11, 2000.

(51) Int. Cl.
*C12N 5/00* (2006.01)
(52) U.S. Cl. ...................................................... 435/325
(58) Field of Classification Search ................. 435/325
See application file for complete search history.

(56) References Cited

OTHER PUBLICATIONS

Romano et al. Journal of Cell Science, 1998, 111: 803-818.*
Golovan et al., *Pigs expressing salivary phytase produce low-phosphorus manure*. Nature Biotechnology, 19: 741-745 (2001).
Golovan et al., *Transgenic mice expressing bacterial phytase as a model for phosphorus pollution control*. Nature Biotechnology, 19: 429-433 (2001).
Scheel, A. et al. "Identification of Amino Acids in the Binding Pocket of the Human KDEL Receptor" J. Biol. Chem., 273(4): 2467-2472, Jan. 1998.

* cited by examiner

*Primary Examiner*—Michael C. Wilson
(74) *Attorney, Agent, or Firm*—Myers Bigel Sibley & Sajovec P.A.

(57) ABSTRACT

The present invention provides an isolated animal cell comprising an exogenous nucleic acid encoding a mutated phytase, wherein the cell produces phytase and secretes the phytase from the cell. The present invention also provides an animal having a phenotype not naturally occurring, characterized by secretion of phytase into the lumen of the gastrointestinal tract of the animal, the phenotype being conferred by a transgene contained in the cells of the animal, the transgene comprising a nucleic acid sequence encoding phytase and methods of making said animal.

8 Claims, No Drawings

USE OF A TRANSGENE ENCODING A VERTEBRATE PHYTASE TO INCREASE CAPACITY TO UTILIZE PHYTIC ACID IN LIVESTOCK FEED

RELATED APPLICATIONS

The present application is an application under 35 USC Section 371 of International Application Serial No. PCT/US01/25339, filed 13 Aug. 2001, which in turn claims the benefit of Provisional Application Ser. No. 60/224,496, filed 11 Aug. 2000, the disclosures of which are incorporated by reference herein as if set forth fully.

BACKGROUND OF THE INVENTION

1. Field of the Invention

The present invention relates to the field of gene transfer and methods of producing animals that express a transgene. Specifically, the present invention provides methods of producing animals that express exogenous nucleic acid encoding phytase, whereby the production of phytase in the animals reduces the need for phosphorus supplementation in the animals' diet. Moreover, the invention provides animals expressing the transgene encoding phytase.

2. Background Art

Phosphorous is an essential animal nutrient and is abundant in animal feed in the form of the plant compound, phytic acid, which is inositol hexaphosphate. Because animals lack the intestinal enzyme required to release phosphorous from phytic acid, undigested phytic acid is excreted into the environment where it is digested by bacteria which release phosphorous which pollutes lakes and rivers and contributes to toxic algal blooms. Moreover, since animals cannot derive phosphorous from phytic acid, animal feed must be supplemented with phosphorous. Adding phosphorous to animal feed increases phosphorous content of animal waste, compounding the problem of pollution, and is also depleting the earth's phosphorous reserves.

The present invention overcomes the problems associated with the lack of the intestinal enzyme required for digesting phytic acid by providing animals capable of utilizing phytic acid in their diet.

SUMMARY OF THE INVENTION

The present invention provides an isolated animal cell comprising an exogenous nucleic acid encoding phytase, wherein the cell expresses the nucleic acid encoding phytase and secretes phytase from the cell.

The present invention further provides an animal having a phenotype not naturally occurring, characterized by secretion of phytase into the lumen of the gastrointestinal tract of the animal, the phenotype being conferred by a transgene contained in cells of the animal, the transgene comprising a nucleic acid encoding phytase.

The present invention also provides a method of producing an animal having a phenotype not naturally occurring, characterized by secretion of phytase into the lumen of the gastrointestinal tract of the animal, comprising introducing at least one transgene into an embryo of the animal, the transgene comprising a nucleic acid encoding phytase, transplanting the embryo into a pseudopregnant animal, allowing the embryo to develop to term and identifying at least one offspring expressing the transgene.

Further, the present invention provides a method of producing a bird having a phenotype not naturally occurring, characterized by secretion of phytase into the lumen of the gastrointestinal tract of the bird, comprising introducing at least one transgene into an embryo of a bird, the transgene comprising a nucleic acid encoding phytase, allowing the embryo to mature into a chick within an egg, allowing the chick to hatch from the egg and identifying a bird expressing the transgene.

DETAILED DESCRIPTION OF THE INVENTION

As used herein, "a," "an" and "the" may mean one or more than one. For example, "an" animal may mean one animal or more than one animal. Moreover, "the" animal may mean one animal or more than one animal.

The present invention provides an isolated animal cell comprising an exogenous nucleic acid encoding phytase, wherein the cell expresses the exogenous nucleic acid to produce phytase and secretes phytase from the cell. "Isolated" as used herein means the cell of the present invention is sufficiently free of contaminants or other cell types with which cells normally occur and is present in such concentration as to be the only significant cell type present in the sample. The cell of the present invention can be in vitro, ex vivo or in vivo.

The cell of the present invention can be any cell of the animal. For example, the cell can be from skin, brain, blood, the respiratory tract or the urogenital tract of an animal. Further, a cell can be from the gastrointestinal tract of an animal, including a cell from the mouth, esophagus, stomach, small intestine and large intestine.

An "exogenous nucleic acid" as used herein means an isolated nucleic acid which can be DNA or RNA, originating in a cell in one animal of a species and introduced into a cell in a host (recipient) animal of the same species. If ex vivo methods are employed, cells or tissues can be removed and maintained outside the body according to standard protocols well known in the art.

It is contemplated by the present invention that the exogenous nucleic acid can be incorporated into the nucleic acid of the cells of the host animal and be functionally expressed. The exogenous nucleic acid can also be present in the host cell as a stably maintained episome which is functionally expressed.

The exogenous nucleic acid of this invention can encode phytase. Phytase is an enzyme produced in a variety of avian (bird) and mammalian tissues which is not normally secreted from cells. In mammals, the enzyme is multiple inositol polyphosphate phosphatase (MIPP) (Craxton et al., (1997), "Molecular cloning and expression of a rat hepatic multiple inositol polyphosphate phosphatase," *Biochem. J.*, 328: 75-81), and in birds, the enzyme is histidine phosphatase of the endoplasmic reticulum (HiPER1). HiPER1 and MIPP remove the phosphate group from inositol 1,3,4,5,6-pentakisphosphate ($InsP_5$) and inositol hexakisphosphate ($InsP_6$) and are compartmentalized in the endoplasmic reticulum (ER) lumen.

The nucleic acids of this invention can also be utilized for in vivo gene therapy techniques (U.S. Pat. No. 5,399,346). With regard to gene therapy applications, the nucleic acid can comprise a nucleotide sequence which encodes a gene product which is meant to function in the place of a defective gene product and restore normal function to a cell which functioned abnormally due to the defective gene product. Alternatively, the nucleic acid may encode a gene product which was not previously present in a cell or was not previously present in the cell at a therapeutic concentration, whereby the presence of the exogenous gene product or increased concentration of the exogenous gene product imparts a therapeutic benefit to the cell and/or to a subject.

Therefore, another embodiment of the present invention provides a method of introducing an exogenous nucleic acid encoding phytase into a cell of an animal, whereby the nucleic acid is expressed in the cell and phytase is produced by and secreted from the cell. Further, the present invention provides an animal expressing an exogenous nucleic acid encoding phytase, said animal producing phytase that is secreted from cells.

For in vivo administration, the cells can be in a subject and the nucleic acid can be administered in a pharmaceutically acceptable carrier. The subject can be any animal in which it is desirable to selectively express a nucleic acid in a cell.

In the method described above which includes the introduction of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid inside the cell. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a Sonoporation machine (ImaRx Pharmaceutical Corp., Tucson, Ariz.).

As one example, vector delivery can be via a viral system, such as a retroviral vector system which can package a recombinant retroviral genome. The recombinant retrovirus can then be used to infect and thereby deliver nucleic acid to the infected cells. The exact method of introducing the nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors, and pox virus vectors, such as vaccinia virus vectors. Physical transduction techniques can also be used, such as liposome delivery and receptor-mediated and other endocytosis mechanism. This invention can be used in conjunction with any of these or other commonly used gene transfer methods.

The nucleic acid and the nucleic acid delivery vehicles of this invention, (e.g., viruses; liposomes, plasmids, vectors) can be in a pharmaceutically acceptable carrier for in vivo administration to a subject. By "pharmaceutically acceptable" is meant a material that is not biologically or otherwise undesirable, i.e., the material may be administered to a subject, along with the nucleic acid or vehicle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acids of this invention can be introduced into the cells via any nucleic acid delivery mechanism, such as, for example, virus-mediated nucleic acid delivery, calcium phosphate mediated nucleic acid delivery, electroporation, microinjection and/or proteoliposomes. The cells comprising the exogenous nucleic acid can then be infused (e.g., in a pharmaceutically acceptable carrier) or transplanted back into a subject per standard methods for the cell or tissue type. Standard methods are known for transplantation or infusion of various cells into a subject.

The present invention further provides an animal having a phenotype not naturally occurring, characterized by secretion of phytase into the lumen of the gastrointestinal tract of the animal, the phenotype being conferred by a transgene contained in cells of the animal, the transgene comprising a nucleic acid encoding phytase. A "transgene" is an isolated nucleic acid originating in one organism which, after being introduced into a cell of a host (recipient) organism, becomes permanently integrated into the host organism's chromosomes, or exists extrachromosomally. The animal can be transgenic or chimeric. As used herein, a "transgenic" animal is an animal in which all the cells of its body comprise and express an exogenous nucleic acid. A "chimeric" animal is an animal in which at least one but not all of the cells of its body comprise and express an exogenous nucleic acid.

The present invention provides an exogenous nucleic acid construct comprising a transgene encoding phytase which can be introduced into a cell of an animal. In one embodiment, the transgene can encode a mutated phytase. A "mutated phytase" is an enzyme not naturally occurring which has been modified to be secreted from a cell and/or modified to be produced at higher than normal levels and/or modified to be more catalytically active. In animals, naturally occurring phytase is produced in cytosol and retained in the endoplasmic reticulum. Retention of phytase in the endoplasmic reticulum prevents the enzyme from being secreted out of the cell. In particular, a naturally occurring phytase cannot be secreted into the lumen of the gastrointestinal tract, and, therefore, it is not available for digestion of inositol phosphates to make phosphorus available for absorption and use by the animal.

The transgene of the present invention encodes a phytase that is mutated so that the phytase can be released from the endoplasmic reticulum and secreted out of the cell. Examples of such mutations include, but are not limited to, removal of the tetrapeptide at the carboxyl end of the protein. The mutated phytase of the present invention can lack a tetrapeptide at the carboxyl end of the protein. Moreover, the mutated phytase can be produced in cells at higher than normal levels. It is further contemplated that the mutated phytase can have a modification in its active site to increase catalytic activity but retain specificity for inositol phosphates.

In one embodiment of the present invention, any cell of an animal in which the transgene is expressed can constitutively express the phytase transgene and secrete phytase into the extracellular space. For constitutive expression of the phytase transgene, the nucleic acid encoding phytase is placed under the control of a constitutive promoter. Examples of constitutive promoters include, but are not limited to, Cytomegalovirus promoter (CMV), Rous Sarcoma Virus promoter (RSV) and chicken beta-actin promoter.

Alternatively, in another embodiment of the present invention, a particular type of cell can selectively express the phytase transgene and secrete phytase from the cell. Therefore, although the transgene can be present in one or more cell types, a particular cell type can be selected for expression of the phytase transgene by placing the nucleic acid encoding phytase under a cell-specific or inducible promoter. For example, a cell lining the gastrointestinal tract of an animal can selectively express the phytase transgene under the control of a cell-specific promoter. Examples of cell-specific or inducible promoters which can be used in the present invention include, but are not limited to, intestinal alkaline phosphatase promoter (Kim et al. *Am J Physiol* 276(4 Pt 1): G800-G8007(1999)), sucrase-isolmaltase promoter (Tung et al., *Am. J. Physiol.* 273 (1 Pt 1): G83-92 (1997)) and intestinal phopholipase A/lysophospholipase (IPAL) promoter (Taylor et al. *DNA Cell Biol.* 16: 1419-1428 (1997)). The phytase is then secreted from the cell into the lumen of the gastrointestinal tract where the phytase can digest phytic acid, releasing phosphorus for absorption by the gastrointestinal epithelial cells and transport into the circulatory system of the animal.

The cell and/or the animal of the present invention can be avian (bird). Examples of a bird of the present invention include, but are not limited to, a chicken, duck, turkey, rhea, goose, ostrich or pheasant. Moreover, the animal of the present invention can be mammalian. Examples of a mammal include, but are not limited to, pig, cow, sheep, goat, bison, deer, mouse or rat, as well as any other animal in which selective expression of a nucleic acid in a cell can be carried out according to the methods described herein.

The present invention further provides a method of producing an animal having a phenotype not naturally occurring, characterized by secretion of phytase into the lumen of the gastrointestinal tract of the animal, comprising introducing at least one transgene into an embryo of the animal, the transgene comprising a nucleic acid encoding phytase, transplanting the embryo into a pseudopregnant animal, allowing the embryo to develop to term and identifying at least one offspring expressing the transgene. The animal produced by the method of the present invention can be a mammal, examples of which include, but are not limited to, a pig, cow, sheep, goat, bison, deer, mouse or rat. Further, the nucleic acid can encode a mutated phytase, as described herein above. An example of a DNA construct comprising a transgene encoding a mutated phytase is described in the Examples herein.

The transgene can be introduced into an embryo of a mammal by introducing an embryonic stem cell comprising the phytase transgene into the embryo. An "embryonic stem cell" is a multipotential cell derived from an early embryo that is capable of giving rise to somatic cells and germ cells in vitro and in vivo. It is well known in the art that embryonic stem cells (ESCs) were first cultured from mouse embryos using a feeder layer of mouse fibroblasts or media conditioned with buffalo rat liver cells. The established ESC lines from mouse embryos have a characteristic phenotype consisting of a large nucleus, a prominent nucleolus, and relatively little cytoplasm. Such cells can be grown relatively indefinitely using the appropriate culture conditions. They can be induced to differentiate in vitro using retinoic acid or spontaneously by removal of the feeder layer or conditioned media. In addition, these cells can be injected into a mouse blastocyst to form a somatic and germ line chimera. This latter property has allowed mouse ESCs to be used for the production of transgenic mice with specific changes to the genome. (M. Evans et al., *Nature* 292, 154 (1981); G. Martin, *Proc. Natl. Acad. Sci.* USA 78, 7638 (1981); A. Smith et al., *Developmental Biology* 121, 1 (1987); T. Doetschman et al., *Developmental Biology* 127, 224 (1988); A. Handyside et al., *Roux's Arch Dev. Biol.* 198, 48 (1989)).

The active compound that allows for the culture of murine ESCs has been identified as differentiation inhibiting activity (DIA), also known as leukemia inhibitory factor (LIF). (A. Smith, *J. Tiss. Cult. Meth.* 13, 89 (1991); J. Nichols et al., *Development* 110, 1341 (1990)). Recombinant forms of LIF can be used to obtain ESCs from mouse embryos. (S. Pease et al., *Developmental Biology* 141, 344 (1990)).

Subsequent to the work with mouse embryos, several groups have attempted to develop stem cell lines from sheep, pig and cow. A cell line with a stem cell-like appearance has been cultured from porcine embryos using culture conditions similar to that used for the mouse. (M. Evans et al., PCT Publication WO 90/03432; E. Notarianni et al., *J. Reprod. Fert., Suppl.* 41, 51 (1990); J. Piedrahita et al., *Theriogenology* 34, 879 (1990); E. Notarianni et al., *Proceedings of the 4th World Congress on Genetics Applied to Livestock Production*, 58 (Edinburgh, July 1990)). U.S. Pat. No. 5,340,740.

Embryonic stem cells have also been developed for the chicken and have been derived from the unincubated embryo and primordial germ cells. These cells are capable of giving rise to multiple cell types in vitro and in vivo. (U.S. Pat. No. 5,340,740; U.S. Pat. No. 5,656,479; PCT Publications, WO 008132A1, WO 9906534A1, and WO 9906533A1; Pain et al. *Development* 122:2339-2348 (1996), Pain et al., *Cells Tissues Organs* 165:212-219 (2000);Park and Han, *Mol. Reprod. Dev.* 56:475-482 (2000)).

In another embodiment of the present invention, the phytase transgene can be introduced into an embryo of a mammal by introducing a viral nucleic acid comprising a phytase transgene into a cell of the embryo. Viral nucleic acid can be in the form of an intact virion, an infectious clone of a virus or a viral vector comprising viral genes. The viral nucleic acid is introduced into the cell by standard methods, e.g., infection, transfection via lipofection, or electroporation. For example, a cell of a mammalian embryo can be infected with a retrovirus or with retroviral vectors. Infection of both pre- and post-implantation mouse embryos with either wild-type or recombinant retroviruses has been reported (Jaenisch (1976) *Proc. Natl. Acad. Sci.* USA 73:1260-1264; Jaenisch et al. (1981) *Cell* 24:519; Stuhlmann et al. (1984) *Proc. Natl. Acad. Sci.* USA 81:7151; Jahner et al. (1985) *Proc. Natl. Acad Sci.* USA 82:6927-6931; Van der Putten, et al. (1985) *Proc. Natl. Acad Sci.* USA 82:6148-6152; Stewart, et al. (1987) *EMBO J.* 6:383-388). The resulting animals are typically mosaic for the transgene since incorporation occurs only in a subset of cells in the animal. An animal which is mosaic for the transgene is a chimeric animal of the present invention.

In addition to the production of chimeric animals, infection of embryos with retrovirus (which is typically performed using embryos at the 8 cell stage or later) can result in the production of animals containing multiple copies of the retroviral provirus at different positions in the genome which generally will segregate in the offspring. Infection of early mouse embryos by co-culturing early embryos with cells producing retroviruses requires enzymatic treatment to remove the zona pellucida (Hogan et al. (1994) in Manipulating the Mouse Embryo: A Laboratory Manual, 2nd Ed., Cold Spring Harbor Laboratory Press, Cold Spring Harbor, N.Y., pp. 251-252). In contrast to mouse embryos, bovine embryos dissociate when removed from the zona pellucida. Therefore, infection protocols which remove the zona pellucida cannot be employed for the production of transgenic cattle or other animals whose embryos dissociate or suffer a significant decrease in viability upon removal of the zona pellucida.

An alternative means for infecting embryos with retroviruses is the injection of virus or virus-producing cells into the blastocoele of embryos (Jahner, D. et al. (1982) *Nature* 298:623-628). As is the case for infection of eight cell stage embryos, most of the animals produced by injection into the blastocoele will be chimeric. The introduction of transgenes into the germline of mice has been reported using intrauterine retroviral infection of the midgestation mouse embryo (Jahner, D. et al. (1982) supra).

Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Publication WO 90/08832 (1990); Haskell and Bowen (1995) *Mol. Reprod. Dev.* 40:386). PCT International Application WO 90/08832 describes the injection of wild-type feline leukemia virus B into the perivitelline space of sheep embryos at the 2 to 8 cell stage. Fetuses derived from injected embryos were shown to contain multiple sites of integration. The efficiency of producing transgenic sheep was 4.2% (efficiency is defined as the number of transgenics produced compared to the number of embryos manipulated).

Haskell and Bowen (supra) describe the micro-injection of mitomycin C-treated cells producing retrovirus into the perivitelline space of 1 to 4 cell bovine embryos. The use of virus-producing cells precludes the delivery of a controlled amount of viral particles per embryo. The resulting fetuses contained between 2 and 12 proviruses and were shown to be mosaic for proviral integration sites, the presence of provirus, or both. The efficiency of producing transgenic bovine embryos was 7%.

In a further embodiment of this invention, the introduction of a phytase transgene into a mammalian embryo can be by direct DNA injection into a pronucleus of a fertilized ovum. (Wall et al., (1992), *J. Cell. Biochem.*, 49: 113). U.S. Pat. No. 6,080,912.

The present invention also provides a transgenic or chimeric animal produced by the method of introducing a transgene into an embryo by introducing an embryonic stem cell comprising the phytase transgene into the embryo. Further, the present invention provides a transgenic or chimeric animal produced by introducing a transgene encoding phytase into a developing embryo by introducing a viral nucleic acid comprising the phytase transgene into a cell of the embryo. Moreover, the present invention provides a transgenic or chimeric animal produced by the introduction of the phytase transgene into an embryo by DNA injection into a pronucleus of a fertilized ovum.

Moreover, the present invention provides a method of producing a transgenic or chimeric bird having a phenotype not naturally occurring, characterized by secretion of phytase into the lumen of the gastrointestinal tract of the bird, comprising introducing an embryonic stem cell, comprising an exogenous nucleic acid encoding phytase (transgene), into an embryo of a bird, allowing the embryo to mature into a chick within an egg, allowing the chick to hatch from the egg and identifying a bird expressing the transgene.

To produce an embryonic stem cell comprising an exogenous nucleic acid encoding phytase, the nucleic acid can be introduced into the avian embryonic stem cell in vitro via standard methods known in the art (e.g., transfection or transduction). The cell comprising the transgene is then injected into an egg (in ovo injection) containing an embryonic bird (e.g., into the yolk sac or onto the chorioallantoic membrane, preferably into the subgerminal cavity, and preferably during early embryonic development (e.g., prior to day 2 or 3 of incubation, and most preferably prior to day 1 of incubation)), with the exogenous nucleic acid encoding phytase being effective to cause a change in phenotype in the bird after hatch (e.g., secreting phytase). Preferably, the egg into which the phytase transgene is introduced is incubated to hatch, and the bird so produced is raised to at least an age at which the change in phenotype is detectable. It is of no deleterious consequence if the transformed embryo and bird are chimeric, provided that a physiological response is achieved in the animal after hatch sufficient to evoke the phenotypic change sought, for example, secreting phytase into the lumen of the gastrointestinal tract.

The mechanism of in ovo injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

A high speed automated injection system for avian embryos is available for practicing the present invention. Numerous such devices are available, for example, the EMBREX INOVOJECT™ system (described in U.S. Pat. Nos. 4,681,063 and 4,903,625 issued to Hebrank), and U.S. Pat. Nos. 4,040,388, 4,469,047, and 4,593,646 issued to Miller. All such devices, as adapted for practicing the present invention, comprise an injector containing the embryonic stem cell as described herein, with the injector positioned to inject an egg carried by the apparatus with the nucleic acid. In addition, a sealing apparatus operatively associated with the injection apparatus may be provided for sealing the hole in the egg after injection thereof.

The exogenous nucleic acid introduced in ovo can be a construct comprising a promoter functional in avian cells and a nucleotide sequence encoding phytase. Preferably, the phytase is physiologically active and capable of being secreted into the lumen of the gastrointestinal tract in the bird. The nucleic acid construct can be a linear DNA sequence (introduced into the embryonic stem cells of the invention by electroporation) or a nucleic acid sequence carried by a vector or other suitable carrier for introducing nucleic acid into the embryonic stem cells of the invention, such as liposomes, calcium phosphate, or DMSO.

A vector of this invention can be a replicable nucleic acid used herein to either amplify and/or express nucleic acid encoding a protein of interest. A suitable vector will have controlling elements capable of expressing the cloned cDNA or genomic DNA placed in the correct orientation when the vector is introduced into the correct host. Such elements typically include, but are not limited to, a promoter region which interacts specifically with cellular proteins involved in transcription, enhancer elements which can stimulate transcription many-fold from linked heterologous promoters, a splice acceptor and/or donor sequences, and termination and polyadenylation signals. Also included is a sequence for a ribosome binding site capable of permitting translation, which is operably linked to the nucleic acid to be expressed. Vectors of this invention can include, but are not limited to, plasmids, viruses (e.g., retrovirus, adenovirus, adeno-associated virus), phage, and/or nucleic acid fragments integratable into the host genome by recombination. The vector can replicate and function independently of the host genome, or it can integrate into the host genome.

The production of cloned genes, recombinant DNA, vectors, transformed host cells, proteins and protein fragments by genetic engineering is well known. See e.g., U.S. Pat. No. 4,761,371 to Bell et al. at Col. 6 line 3 to Col 9 line 65; U.S. Pat. No. 4,877,729 to Clark et al. at Col. 4 line 38 to Col 7 line 6; U.S. Pat. No. 4,912,038 to Schilling at Col. 3 line 26 to Col. 14 line 12. Protocols for restriction endonuclease digestion, preparation of vectors, DNA purification and other such procedures were essentially as described in standard cloning manuals. See Sambrook et al., Molecular Cloning, a Laboratory Manual, (2d Ed., Cold Spring Harbor Press, New York (1989)).

The present invention further provides a bird produced by any and all of the methods of this invention as described herein. The bird produced by the methods of the present invention can be transgenic or chimeric.

The present invention is more particularly described in the following examples which are intended as illustrative only since numerous modifications and variations therein will be apparent to those skilled in the art.

EXAMPLES

Example 1

HiPER1 Constructions: I

The first two plasmids to be assayed for secreted phytase activity were pRO483, which contains the entire coding sequence of HiPER1 (Romano et al., (1998), "HiPER1, a phosphatase of the endoplasmic reticulum with a role in chondrocyte maturation," *Journal of Cell Science*, 111:803-813), and pRO501, which contains all but the final 5 amino acids, VADEL (SEQ ID NO:5). In both plasmids, expression is driven by a cytomegalovirus (CMV) promoter, which is a common promoter used for non-specific expression in higher eukaryotic cells. The vectors were purchased from Invitrogen. In pRO483, a 2.1 kb Bam HI-EcorI site containing ~60 bp of 5' untranslated region (UTR), 1447 bp of coding sequence, and ~600 bp of 3' UTR were cloned into pcDNA 3.1+. The upstream Bam HI site is designated by an asterisk on page 2-front. (The downstream EcorI is beyond the sequence on page 2-f.)

In pRO501, a 1.4 kb NotI to KpnI fragment (*) in Page 2-f) was cloned into identical sites in pcDNA 3.1 (–) Myc-ltis-A, replacing the amino acids Valine-Alanine-Aspartate-Glutamate-Leucine (VADEL) (SEQ ID NO:5) with the myc epitope and six histidines (His6) (SEQ ID NO:6). The myc epitope is for antibody detection and the His$_6$ (SEQ ID NO:6) is for purification. Additionally, the VADEL (SEQ ID NO:5) sequence that is removed includes the carboxyl terminal sequence which, in both HiPER1 and MIPP, causes retention of the protein in the endoplasmic reticulum (Pelham, *Trends in Biochem. Sciences*, Vol. 15, pages 483-486). The mutated protein is therefore secreted.

HiPER1 Constructions: II

The third construction involved rotating part of the HiPER1 sequence within pRO501. The yeast phytases have a very high rate of activity on phytic acid, relatively higher than HiPER1. HiPER1 has conservation of the active site Arg-His-Gly (RHG)(SEQ ID NO:8), but at a downstream sequence known to be part of the active site, HiPER1 has the amino acid sequence His-Ala-Glu-Thr (HAET)(SEQ ID NO:7) where the yeast enzymes have the amino acid sequence His-Asp-Thr (HDT)(SEQ ID NO:9). Glutamate and Aspartate both have carboxyl side chains, so it appears that in HiPER1, the carboxyl group has been "displaced" by one amino acid. In vitro mutagenesis by PCR was performed to change the HiPER1 sequence to HDT (SEQ ID NO:9). Two fragments were amplified with primer pairs A+B and C+D. (B+C contain the mutated sequence, and overlap). The two PCR products were denatured, annealed, and amplified with primers A+D. The resulting fragment contains the mutated sequence. The PCR product was cut with EcoRV and KpnI, and ligated into pRO501 that had been gapped with EcoRV and KpnI. This created plasmids pRO591 and pRO592. The following are the primers used herein:

```
                                              (SEQ ID NO:1)
Primer A: CTGGAGTACCTGAATGACC
A:
                                              (SEQ ID NO:2)
Primer B: AAGTGTGTCATGACCAACTTGTACAATC (SEQ ID NO:3)
Primer C: GTTGGTCATGACACACTTCAGCCACTTCTTG (SEQ ID NO:4)
Primer D: CCTCAAAGTTCGTCAGCAAC.
```

HiPER1 Constructions: III

The vector pmiΔZ was constructed by digesting pmiwZ (Suemori et al., (1990), *Cell Differentiation and Development*, 29:181-186) with BamHI and self-ligated. This provided a chicken beta-actin, RVS tandem promoters with a delta crystalline enhancer. The expression vector, pmiΔZ, was modified at the sequence around the initiation codon (ATG) so that the ATG would be within an NCOI site (CC ATGG) followed by an EcorV (GATATC) site, then the BamHI and KpnI sites from the vector. The mutated pmiΔZ vector was called pRO593.

The wild type sequence from pRO483, the secretion construction in pRO501, and the HDT (SEQ ID NO:9)-secretion construction in pRO592 were all respectively cloned into pRO593. Each of the fragments was cloned as an NOOI-PmeI fragment. NOOI brackets the ATG of HiPER1 (underline, Page 1-f). The PmeI is found downstream of the multiple cloning site in the pcDNA vectors. The new plasmids were called pRO594, (wt seq), pRO595 (secr.), and pRO596 (HDT (SEQ ID NO:9)-Secr).

Example 2

LMH Transfection 1. 4×10$^6$ LMH cells (chicken liver cell line, ATCC #CLR-2117) are seeded in a 75 cm$^2$ tissue culture flask (4 flasks are initiated per plasmid). Cells are incubated overnight at 37° C./5% CO$_2$.
2. 24 hours later, the following prepare transfection mixture is prepared (plasmid/Superfect™ mixture): For each flask, add 32 μg of plasmid to 800 μl OptiMEM (Gibco) in a 1.5 ml microcentrifuge tube and mix by passing through the pipette tip. Incubate 5 minutes at room temperature. Add 64 μl Superfect™ (Qiagen) to the tube and mix by gentle passage through the pipette tip. Incubate 15 minutes at room temperature.
3. Remove media from LMH cells and wash once with PBS (Phosphate Buffered Saline).
4. Add the plasmid/Superfect mixture to 4.8 ml DMEM/10% FBS in a 12×75 mm polystyrene tube. Mix by inversion and add to the washed LMH cells.
5. Incubate 2.5 hours at 37° C./5% $CO_2$.
6. Add 10 ml DMEM/10% FBS to each flask and continue incubation for 72 hours.
7. After 72 hours of incubation, remove media and wash the cells 3 times with PBS. Add 20 ml DMEM to each flask and incubate 48 hours at 37° C./5% $CO_2$.
8. Media from 4 flasks is pooled and concentrated to approximately 5 ml with a Centricon Plus-80 centrifugal filter device.

Phytase Assay

The phytase activity in an extract of biological material is assayed by incubating the material at 37 degrees centigrade, with tritium-radiolabeled phytic acid in an assay medium consisting of 1 mM magnesium chloride, 50 mM HEPES buffer (pH 7.0), 50 mM potassium chloride. After an appropriate time (between 10 and 60 min) the assays are stopped by addition of 0.2 volumes of ice-cold 2M perchloric acid and then neutralized with 0.05 volumes of ice-cold 1 M potassium carbonate. Samples are transferred to centrifuge tubes and centrifuged for 2 min at approx 10,000×g to remove the insoluble perchlorate precipitate. The supernatant is saved and analyzed by high performance liquid chromatography; in this procedure, an anion-exchange column is used to separate phytic acid from the less highly polar breakdown products that accumulate when phytic acid is hydrolyzed by phytase. Details of this procedure are described in detail in an article by S. B. Shears, pp33-52, in "Signaling By Inositides: A Practical Approach" ed S. B. Shears IRL Press, Oxford, 1997.

The media from wild-type and transfected cells were incubated with $^3$H-labeled phytic acid. After appropriate times, the reactions were quenched, and the extracts were analyzed by high performance liquid chromatography. Phytase activity was assayed from the degree of breakdown products of $^3$H-phytic acid. Media from wild-type cells had very low levels of phytase activity that were only just above the level of detection. The media from transfected cells had 1000-2000 fold greater phytase activity. Thus, considerable quantities of phytase were secreted.

Example 3

Avian Embryonic Stem Cell Culture:
1. 16-24 hours before embryo isolation, prepare gamma irradiated STO feeders in gelatinized 6 or 12 well tissue culture plates. STO is an immortalized fibroblast cell line. I-STO: Irradiated STO (ATCC# CRL-1503 or CRL-2225).
2. Immediately prior to embryo isolation, replace feeder medium with CES-80, Buffalo Rat Liver (BRL) (ATCC# 1442).
3. Isolate blastodermal cells from the area pellucida of stage X embryos.
4. Once enough embryos are collected (20-40 depending on well size), gently pipet the PBS-G/embryo mixture 4-5 times with a p1000 Pipetman™ to disperse the cells.
5. Centrifuge at 300×g in a variable speed microcentrifuge for 5 minutes, remove supernatant and discard.
6. Add 300-600 µl CES-80 to the pellet and resuspend.
7. Seed onto the previously prepared feeders and incubate at 37° C., 5% $CO_2$
   Amount to seed: 12-well plate—100,000-140,000
       6-well plate—230,000-300,000
8. Replace medium each day (2.5 ml/12-well plate, 6 ml/6-well plate).
9. Pass cells when embryonic stem cell colonies are prominent and the feeder layer is deteriorating. A new I-STO feeder must be seeded 1 day prior to passage.
10. Passage: Remove medium and wash cells twice with PBS. Add ice cold 1×Trypsin/EDTA solution (0.05% Trypsin, 0.53 mM EDTA) to the well (100 µl for 12 well plate and 250 ul for 6 well plate). Immediately observe under a microscope. When the ES like cells begin to detach (30 seconds-2 minutes, add CES-80 (1 ml for 12-well plate, 2.5 ml for 6-well plate) and aspirate the cells off the dish bottom. Split the cell suspension to 2 new I-STO feeders (prepared the day before) and incubate. U.S. Pat. No. 5,656,479 and U.S. Pat. No. 5,340,740.

Transfection of Avian Embryonic Stem cells:
1. Wash culture plate 2 times with PBS-G.
2. Prepare liposome/DNA (DNA/Superfect™) complex: In a 0.5 ml tube, add 10 µl Superfect™ to 140 ul OptiMEM™ (Gibco/BRL). Mix and add 2 µg plasmid DNA. Mix and incubate 10 minutes at room temperature.
3. To the cells, add the DNA/Superfect complex and mix by gentle pipetting (3-4 times). Incubate cells at 37° C./5% $CO_2$ 3-24 hours.
4. Replace medium with CES-80
5. If using puromycin-resistant STO cells, select cells with 5 µg puromycin per ml of CES-80.

Production of Avian Chimeras:

(Based upon Petitte et al., 1990 and Carsience et al., 1993)
1. Identify individual colonies of avian embryonic stem cells and isolate them from the plate using microdissection.
2. Pool the colonies and gently disperse in 500 µl DMEM.
3. Prepare recipient embryos using the surrogate eggshell system.
4. Inject 500-2000 cells into the subgerminal cavity of an unincubated embryo. Seal egg for surrogate eggshell system.

Surrogate Eggshell System (Based upon Perry 1988 and Rowlett and Simkiss, 1987)

Preparing Eggs for Surrogate Eggshell Culture: System II

Obtain enough chicken eggs for recipient embryos and recipient shells.
1. Choose recipient eggs weighing 3-4 g more than the recipient embryo egg.
2. Recipient shell eggs should have their pointed ends marked in pencil using a 32 mm circle template as a guide.
3. Gamma irradiate the recipient embryo eggs and place them pointed end down in an egg tray for a minimum of 1 hour.
4. Cut the recipient shell eggs along the marked line as smoothly and evenly as possible.
5. After cutting the recipient shells, turn them window down in a clean plastic egg tray to drain.
6. Rinse the empty shells with $dH_2O$. Rinse the outside first with the window down, then gently rinse the inside several times.

7. Remove a set pair (recipient embryo and its recipient shell) from the tray and place the recipient shell into a suitable holder.
8. Gently crack the recipient embryo egg into the catch basin.
9. Pour the recipient embryo gently from the basin into the recipient shell, by tilting the shell to horizontal and rotate up as the embryo enters.
10. Place the now full recipient shell back onto the holder. Make sure the embryo is oriented up towards the window.
11. Injection can proceed at this point.
12. Add enough albumen, if needed, to fill the recipient shell so there is a slight meniscus protruding from above the window
13. Use a Pasteur pipet to remove any small bubbles from the surface of the albumen.
14. Place a small square of handi-wrap or other plastic wrap over the window.
15. Place one PVC ring over the plastic to hold it in place over the window, then place a second PVC ring on the bottom and secure them in place with four rubber bands.
16. Turn the now sealed egg window down and place it in a clean plastic egg tray.
17. Place eggs into an incubator set on 99.5° F. Relative Humidity 60%, with a 90° angle of rotation.
18. Allow eggs to incubate 96 hours, then proceed with System III transfer.

Preparing Eggs for Surrogate Eggshell Culture: System III
1) Prepare surrogate turkey shells that are 40 grams heavier than donor egg from System II.
2) Transfer the egg contents of System II to the System III turkey eggshell.
3) Place the turkey shell with its new contents into a large PVC ring.
4) Using a sterile cotton swab, apply a light coating of albumen around the outside of the window, to act as glue for the plastic wrap.
5) Place the square of plastic wrap over the window, and secure with the PVC clamp apparatus and four rubber bands.
6) Place these eggs in an incubator with a 60° angle of rotation, with the window up.
7) On day 18 these eggs should be moved to a hatcher with baskets, and no rotation.
8) Look for signs of hatching on day 21-22.

REFERENCES

Carsience R S, Clark M E, Verrinder Gibbins A M, and Etches R J. (1993) Germline chimeric chickens from dispersed donor blastodermal cells and compromised recipient embryos. Development 117:669-75.

Perry, M. M. (1988) A complete culture system for the chick embryo. Nature 331:70-72.

Petitte J N, Clark M E, Liu G, Verrinder Gibbins A M, and Etches R J. (1990) Production of somatic and germline chimeras in the chicken by transfer of early blastodermal cells. Development. 108:185-9.

Rowlett, K., and Simkiss, K. (1987). Explanted embryo culture: in vitro and in ovo techniques for the domestic fowl. British Poultry Science, 28:91-101.

Medium: CES-80: (100 ml)
    80 ml BRL (ATCC# 1442) conditioned media, pH 7.5
    10 ml FBS
    8.8 ml DMEM
    0.2 ml 55 mM 2-mercaptoethanol (Gibco/BRL)
    1 ml 100 mM sodium pyruvate (Gibco/BRL)

I-STO : Irradiated STO (ATCC# CRL-1503 or CRL-2225)
1. Culture cells until there are 3-4 T-175 confluent flasks.
2. Dissociate cells with trypsin/EDTA to single cells.
3. Pool cells and irradiate with 400 RADS from a gamma source.
4. Count and freeze cells in DMSO.

Example 4

Transgenic swine expressing a vertebrate phytase gene are produced by microinjection into pronuclei of fertilized embryos, infection with retroviruses or recombinant retroviral vectors or embryonic stein cells, according to procedures well known in the art. For example, porcine embryonic stem cells have been developed that allow for their culture and use in the production of chimeric embryos with or without the introduction of genetic modifications (Wheeler, U.S. Pat. No. 5,942,435). Pseudotyped, recombinant retroviral vectors are used as a means of introducing DNA into the pre-fertilized oocyte, at the pronuclear stage shortly after fertilization and the one-cell zygote of the domestic cow (Bremel et al., U.S. Pat. No. 6,080,913). By this method pseudotpyed retroviral vectors are used to develop a transgenic pig expressing phytase. Such recombinant viral vectors are pseudotyped using the vesicular stomatitis virus G protein (VSV-G), which allows for efficient delivery of virions into the cell of several species, including non-mammals.

Transgenic birds expressing a vertebrate phytase gene are produced by microinjection of a fertilized ovum (Love, et al. 1994), retroviral infection, recombinant retroviral vectors or embryonic stem cells. Transgenic birds are produced using retroviral vectors injected into the unincubated embryo (Salter et al., 1986, 1987, 1993; Bosselman et al., 1989; Bosselman et al., U.S. Pat. No. 5,162,215) or through infection of primordial germ cells (Vick L., Li Y., and Simkiss K. (1993).Transgenic birds from transformed primordial germ cells. Proc R Soc Lond B Biol Sci 251:179-182). VSV-G pseudotyped, replication-incompetent retroviral vectors are used for efficient gene transfer into somatic tissues of the avian embryo (Chen C. M., Smith D. M., Peters M. A., Samson M. E., Zitz J., Tabin C. J., and Cepko C. L. (1999). Production and design of more effective avian replication-incompetent retroviral vectors. Developmental Biology, 214:370-384). These procedures are used to produce, for example, a transgenic chicken that expresses a vertebrate phytase gene.

Example 5

Vector Construction:

Plasmids:

Plasmids pRO483 and pRO501 were used to transfect LMH cells.
O) pIAPsma1 (Kim et al., 1999) contains nucleotides 0 through -521 of the human intestinal alkaline phosphatase gene promoter from pIAPsma1 and substituted for the CMV promoter of pRO595.
P) pIAPsma1 (Kim et al., 1999) contains nucleotides 0 through -521 of the human intestinal alkaline phosphatase gene promoter from pIAPsma1 and substituted for the CMV promoter of pRO595.

Q) pIAPsma1 (Kim et al., 1999) contains nucleotides 0 through -521 of the human intestinal alkaline phosphatase gene promoter from pIAPsma1 (Kim et al., 1999) and substituted for the beta-actin and RSV promoters of pRO594.

R) pIAP595 contains nucleotides 0 through -521 of the human intestinal alkaline phosphatase gene promoter from pIAPsmal (Kim et al., 1999) and substituted for the beta-actin and RSV promoters of pRO594.

S) pIAP596 contains nucleotides 0 through -521 of the human intestinal alkaline phosphatase gene promoter from pIAPsmal (Kim et al., 1999) and substituted for the beta-actin and RSV promoters of pRO594.

All plasmids are used for transfection studies of LMH cells and intestinal cells in vitro and in vivo. Microinjection of the plasmids into mammalian oocytes and avian ova is used for the generation of transgenic animals. All plasmids are transfected into mammalian or avian embryonic stem cells to generate chimeras and transgenic animals.

Viral Vectors:

A) pRIAS is an RSV viral genome with a deleted env gene an intact gag and pol genes and an added splice acceptor site of the src gene (Chen et al., 1999).

B) pRIS483 contains the full length wild type HiPER1 cloned into the unique ClaI site pRAIS.

C) pRIS595 contains HiPER1 with an ADEL deletion cloned into the unique ClaI site pRAIS.

D) PRIA596 contains HiPER1 with an ADEL (SEQ ID NO:10) deletion and a HDT (SEQ ID NO:9) in place of HAET (SEQ ID NO:7) to provide an initiation at the conserved histidine toward the C-terminus of HiPER1.

These vectors are used with the appropriate packaging cell lines to infect cells and tissues in vitro and to develop transgenic animals.

Kim J. H., Meng S., Shei A., Hodin R. A. (1999). A novel Sp1-related cis element involved in intestinal alkaline phosphatase gene transcription. *Am J Physiol* 1999 276(4 Pt 1):G800-G8007.

Incorporation by Reference

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

Other Embodiments

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated animal cell comprising an exogenous nucleic acid encoding phytase, wherein the phytase comprises a mutation, further wherein the mutation comprises a deletion of the C-terminal tetrapeptide, and the nucleic acid encoding phytase is functionally expressed in the cell and the phytase is secreted from the cell.

2. The cell of claim 1, wherein the nucleic acid is DNA.

3. An isolated mammalian cell comprising an exogenous nucleic acid encoding phytase, wherein the phytase is a mutated phytase comprising a deletion of the C-terminal tetrapeptide, and further wherein the cell expresses the nucleic acid encoding phytase and secretes phytase from the cell.

4. The cell of claim 1, wherein the cell is avian.

5. The cell of claim 1, wherein the phytase is a mutated phytase comprising a deletion of the final four amino acids, ADEL (SEQ ID NO: 10), of the C-terminus.

6. An isolated animal cell comprising an exogenous nucleic acid encoding phytase, wherein the phytase is a mutated multiple inositol polyphosphate phosphatase comprising a deletion of the C-terminal tetrapeptide, and further wherein the cell expresses the nucleic acid encoding phytase and secretes phytase from the cell.

7. The cell of claim 4, wherein the phytase is histidine phosphatase of the endoplasmic reticulum.

8. The isolated animal cell of claim 1, wherein the exogenous nucleic acid encoding phytase is under transcriptional control of a cell specific or inducible promoter which regulates expression of the phytase.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial sequence
<220> FEATURE:
<223> OTHER INFORMATION: Synthetic construct

<400> SEQUENCE: 1
ctggagtacc tgaatgacc                                                    19

<210> SEQ ID NO 2
<211> LENGTH: 28
<212> TYPE: DNA
<213> ORGANISM: Artificial sequence
<220> FEATURE:
<223> OTHER INFORMATION: Synthetic construct

<400> SEQUENCE: 2
aagtgtgtca tgaccaactt gtacaatc                                          28

<210> SEQ ID NO 3
<211> LENGTH: 31
<212> TYPE: DNA
<213> ORGANISM: Artificial sequence
<220> FEATURE:
<223> OTHER INFORMATION: Synthetic construct

<400> SEQUENCE: 3
gttggtcatg acacacttca gccacttctt g                                      31
```

```
-continued

<210> SEQ ID NO 4
<211> LENGTH: 20
<212> TYPE: DNA
<213> ORGANISM: Artificial sequence
<220> FEATURE:
<223> OTHER INFORMATION: Synthetic construct

<400> SEQUENCE: 4
cctcaaagtt cgtcagcaac                                               20
```